(12) United States Patent
Faulkner et al.

(10) Patent No.: US 11,103,298 B2
(45) Date of Patent: Aug. 31, 2021

(54) SYSTEMS AND METHODS FOR DETECTING INSERTION OR REMOVAL OF A CABLE

(71) Applicant: COVIDIEN LP, Mansfield, MA (US)

(72) Inventors: William D. Faulkner, Boulder, CO (US); Robert H. Wham, Boulder, CO (US)

(73) Assignee: Covidien LP, Mansfield, MA (US)

( * ) Notice: Subject to any disclaimer, the term of this patent is extended or adjusted under 35 U.S.C. 154(b) by 824 days.

(21) Appl. No.: 15/798,515

(22) Filed: Oct. 31, 2017

(65) Prior Publication Data

US 2019/0125426 A1    May 2, 2019

(51) Int. Cl.
*A61B 18/12*    (2006.01)
*A61B 18/00*    (2006.01)

(52) U.S. Cl.
CPC    *A61B 18/1206* (2013.01); *A61B 2018/00178* (2013.01); *A61B 2018/00666* (2013.01); *A61B 2018/00678* (2013.01); *A61B 2018/00702* (2013.01); *A61B 2018/00827* (2013.01); *A61B 2018/00875* (2013.01); *A61B 2018/00886* (2013.01); *A61B 2018/00892* (2013.01); *A61B 2560/0276* (2013.01)

(58) Field of Classification Search
CPC ...... A61B 18/1206; A61B 2018/00886; A61B 2018/00666; A61B 2018/00827; A61B 2018/00892; A61B 2560/0276; A61B 2018/00875; A61B 2018/00678; A61B 2018/00178; A61B 2018/00702
See application file for complete search history.

(56) References Cited

U.S. PATENT DOCUMENTS

| | | |
|---|---|---|
| 5,493,650 A | 2/1996 | Reinke et al. |
| 7,603,486 B2 | 10/2009 | Le et al. |
| 7,902,810 B2 | 3/2011 | Naylor et al. |
| 8,725,910 B1 | 5/2014 | Sala et al. |
| 8,872,505 B2 | 10/2014 | Furtner |
| 2004/0249991 A1 | 12/2004 | Ali et al. |
| 2011/0152962 A1 | 6/2011 | Behm et al. |
| 2015/0054451 A1 | 2/2015 | Rokusek et al. |
| 2015/0196349 A1* | 7/2015 | Wham ............... A61B 18/1206 606/34 |

(Continued)

*Primary Examiner* — Daniel W Fowler
(74) *Attorney, Agent, or Firm* — Carter, DeLuca & Farrell LLP

(57) ABSTRACT

The disclosed systems and methods relate to detecting coupling or uncoupling of an external cable from an output port of an electrosurgical generator when a cable detection switch is unavailable or inoperable. The electrosurgical generator includes internal cabling having a first end portion connected to the output port and a second end portion. The disclosed technology includes supplying power from the electrosurgical generator, measuring current and voltage at the second end portion of the internal cabling within the electrosurgical generator, accessing one or more parameters associated with internal cable compensation corresponding to the internal cabling within the electrosurgical generator, and determining coupling or uncoupling of an external cable from the output port based on the measured current, the measured voltage, and the one or more parameters associated with internal cable compensation.

13 Claims, 9 Drawing Sheets

(56) References Cited

U.S. PATENT DOCUMENTS

2016/0081739 A1\* 3/2016 Heckel ............... A61B 18/1445
606/34
2016/0270841 A1\* 9/2016 Strobl ................ A61B 18/1206
2017/0325874 A1\* 11/2017 Noack ................ A61B 18/1206

\* cited by examiner

SYSTEMS AND METHODS FOR DETECTING INSERTION OR REMOVAL OF A CABLE

BACKGROUND

1. Technical Field

The present disclosure generally relates to systems and methods for detecting an insertion or removal of a cable from an electrosurgical generator. More particularly, the present disclosure relates to electrosurgical systems and methods for detecting insertion or removal of a cable based on various currents associated with a cable.

2. Background of Related Art

Electrosurgery involves the application of high-frequency electric current to cut or modify biological tissue during an electrosurgical operation. Electrosurgery is performed using an electrosurgical generator, an active electrode, and a return electrode. The electrosurgical generator (also referred to as a power supply or waveform generator) generates power. At least a portion of that power is applied to a patient's tissue through the active electrode, and part of the applied power is then returned to the electrosurgical generator through the return electrode. The power supplied by the generator typically is AC and has a frequency above 100 kilohertz (kHz) to avoid muscle and/or nerve stimulation.

The two main modes of electrosurgery are monopolar and bipolar electrosurgery. Both of these modes of electrosurgery use an active electrode and a return electrode, but the two modes usually involve different numbers of cables. For example, monopolar electrosurgery generally involves connecting two cables to the generator, whereas bipolar electrosurgery generally involves connecting one cable to the generator. When the cable or cables are connected to the electrosurgical generator, the energy can be provided to the cable(s). Many generators have a switch for detecting insertion or removal of a cable from the electrosurgical generator. Such a switch can enable an electrosurgical generator to automatically perform certain functions when a cable insertion or removal is detected by the switch. However, if there is no such switch or if the switch is inoperable or unavailable, those electrosurgical generator functions would need to be manually controlled by an operator or medical professional, which would undesirably divert their attention from the patient. Thus, there is continuing interest in developing technology that enables an electrosurgical generator to determine insertion and/or removal of a cable and to automatically control supply of electrosurgical energy through the cable.

SUMMARY

The electrosurgical systems and methods of the present disclosure relate to determining whether an external cable is coupled to or uncoupled from an electrosurgical generator when a cable detection switch is unavailable or inoperable.

In one aspect, the disclosed method includes supplying power from the electrosurgical generator, which includes internal cabling having a first end portion connected to the output port and a second end portion, measuring current and voltage at the second end portion of the internal cabling within the electrosurgical generator, accessing one or more parameters associated with internal cable compensation corresponding to the internal cabling within the electrosurgical generator, and determining coupling or uncoupling of an external cable from the output port based on the measured current, the measured voltage, and the one or more parameters associated with internal cable compensation.

In various embodiments, the internal cabling includes a resistance, an inductance, a capacitance, and a leakage capacitance, and the one or more parameters include one or more of an impedance corresponding to the resistance, the inductance, and the capacitance, or an impedance corresponding to the leakage capacitance.

In various embodiments, determining coupling or uncoupling of the external cable from the output port includes applying the internal cable compensation to estimate current at the output port based on the measured current, the measured voltage, and the one or more parameters. The method further includes comparing the estimated current at the output port to a current threshold, and determining coupling or uncoupling of the external cable from the output port based on the comparison. In various embodiments, the current threshold is between 5 mA and 10 mA, inclusive.

In various embodiments, comparing the estimated current at the output port includes determining that the estimated current at the output port is greater than the current threshold. The disclosed method determines that the external cable is coupled when the estimated current at the output port has been greater than the current threshold for a predetermined period of time.

In various embodiments, comparing the estimated current at the output port includes determining that the estimated current at the output port is less than the current threshold. The disclosed method determines that the external cable is uncoupled when the estimated current at the output port has been less than the current threshold for a predetermined period of time.

In various embodiments, supplying power from the electrosurgical generator includes applying an interrogation voltage signal. In various embodiments, the frequency of the interrogation voltage signal is substantially the same as the frequency of therapeutic treatment energy that is to be supplied by the electrosurgical generator. In various embodiments, the amplitude of the interrogation voltage signal is less than the amplitude of the therapeutic treatment energy.

In various embodiments, the external cable is coupled to the output port of the electrosurgical generator through an adaptor. In various embodiments, the estimated current at the output port is an estimate of current passing through the adaptor.

In an aspect of the present disclosure, the disclosed electrosurgical generator includes a power supply, an output port configured to receive an external cable, internal cabling having a first end portion connected to the output port and a second end portion, a current sensor configured to measure current at the second end portion of the internal cabling, and a voltage sensor configured to measure voltage at the second end portion of the internal cabling. The electrosurgical generator also includes one or more processors, and at least one memory coupled to the one or more processors and storing instructions which, when executed by the one or more processors, cause the electrosurgical generator to supply power from the power supply, receive a current measurement from the current sensor, receive a voltage measurement from the voltage sensor, access one or more parameters associated with internal cable compensation corresponding to the internal cabling within the electrosurgical generator, and determine coupling or uncoupling of the external cable from the output port based on the current measurement, the voltage measurement, and the one or more parameters associated with internal cable compensation.

In various embodiments, the internal cabling includes a resistance, an inductance, a capacitance, and a leakage capacitance, and the one or more parameters include one or more of an impedance corresponding to the resistance, the inductance, and the capacitance, or an impedance corresponding to the leakage capacitance. For determining coupling or uncoupling of the external cable from the output port, the memory stores further instructions which, when executed by the one or more processors, cause the electrosurgical generator to apply the internal cable compensation to estimate current at the output port based on the measured current, the measured voltage, and the one or more parameters. The memory stores further instructions which, when executed by the one or more processors, cause the electrosurgical generator to compare the estimated current at the output port to a current threshold, and determine coupling or uncoupling of the external cable from the output port based on the comparison. In various embodiments, the current threshold is between 5 mA and 10 mA, inclusive.

In various embodiments, for comparing the estimated current at the output port, the memory stores further instructions which, when executed by the one or more processors, cause the electrosurgical generator to determine that the estimated current at the output port is greater than the current threshold. In various embodiments, for determining coupling or uncoupling of the external cable from the output port, the memory stores further instructions which, when executed by the one or more processors, cause the electrosurgical generator to determine that the external cable is coupled when the estimated current at the output port has been greater than the current threshold for a predetermined period of time.

In various embodiments, for comparing the estimated current at the output port, the memory stores further instructions which, when executed by the one or more processors, cause the electrosurgical generator to determine that the estimated current at the output port is less than the current threshold. In various embodiments, for determining coupling or uncoupling of the external cable from the output port, the memory stores further instructions which, when executed by the one or more processors, cause the electrosurgical generator to determine that the external cable is uncoupled when the estimated current at the output port has been less than the current threshold for a predetermined period of time.

In various embodiments, the electrosurgical generator further includes an adaptor configured to be connected between the output port and the external cable. The estimated current at the output port is an estimate of current passing through the adaptor.

In various embodiments, the supplied power from the electrosurgical generator is an interrogation voltage signal. In various embodiments, the frequency of the interrogation voltage signal is substantially the same as the frequency of therapeutic treatment energy that is to be supplied by the electrosurgical generator. In various embodiments, the amplitude of the interrogation voltage signal is less than the amplitude of the therapeutic treatment energy.

BRIEF DESCRIPTION OF THE DRAWINGS

Various embodiments of the present disclosure are described with reference to the accompanying drawings wherein.

DETAILED DESCRIPTION

The present disclosure relates to detecting whether a cable is coupled to or uncoupled from an electrosurgical generator when a cable-detection switch is unavailable or inoperable. As will be described herein in more detail, the disclosed technology measures or estimates the amount of current at various points of an electrosurgical system, and determines cable insertion or removal based on the measured or estimated current.

Leakage current caused by a cable generally relates to small amounts of current that a cable may draw from an electrosurgical generator separate and apart from any current that a device or instrument may actively draw through the cable. Leakage current typically occurs when the layout of electrical components in a cable provides unintended electrical effects, such as a capacitive effect at a cable location where there is no capacitor. Such unintended electrical effects can be referred to as "parasitic" effects. With parasitic capacitance, for example, a cable can draw a small amount of current from the electrosurgical generator because current would flow through the parasitic capacitance as though it were an actual capacitor. These parasitic effects alter the power supplied by an electrosurgical generator, such that the treatment energy ultimately applied to a patient may not match the generator settings.

An electrosurgical generator can employ compensation techniques that account for the parasitic effects in cables. These compensation techniques involve determining and storing electrical parameters for cables, such as series inductance, shunt capacitance, and resistance. These compensation techniques may include internal cable compensation, which compensates for parasitics of cables inside the electrosurgical generator, and external cable compensation, which compensates for parasitics in cables that are external to and that couple to the electrosurgical generator.

The electrosurgical systems and methods of the present disclosure employ internal and external cable compensation in particular ways. The disclosed systems and methods employ internal and external cable compensation during treatment of a patient. In accordance with embodiments of the present disclosure, when detecting an insertion or removal of a cable, the electrosurgical systems and methods utilize the internal cable compensation but not the external cable compensation, as will be described in more detail herein.

Figure 1:
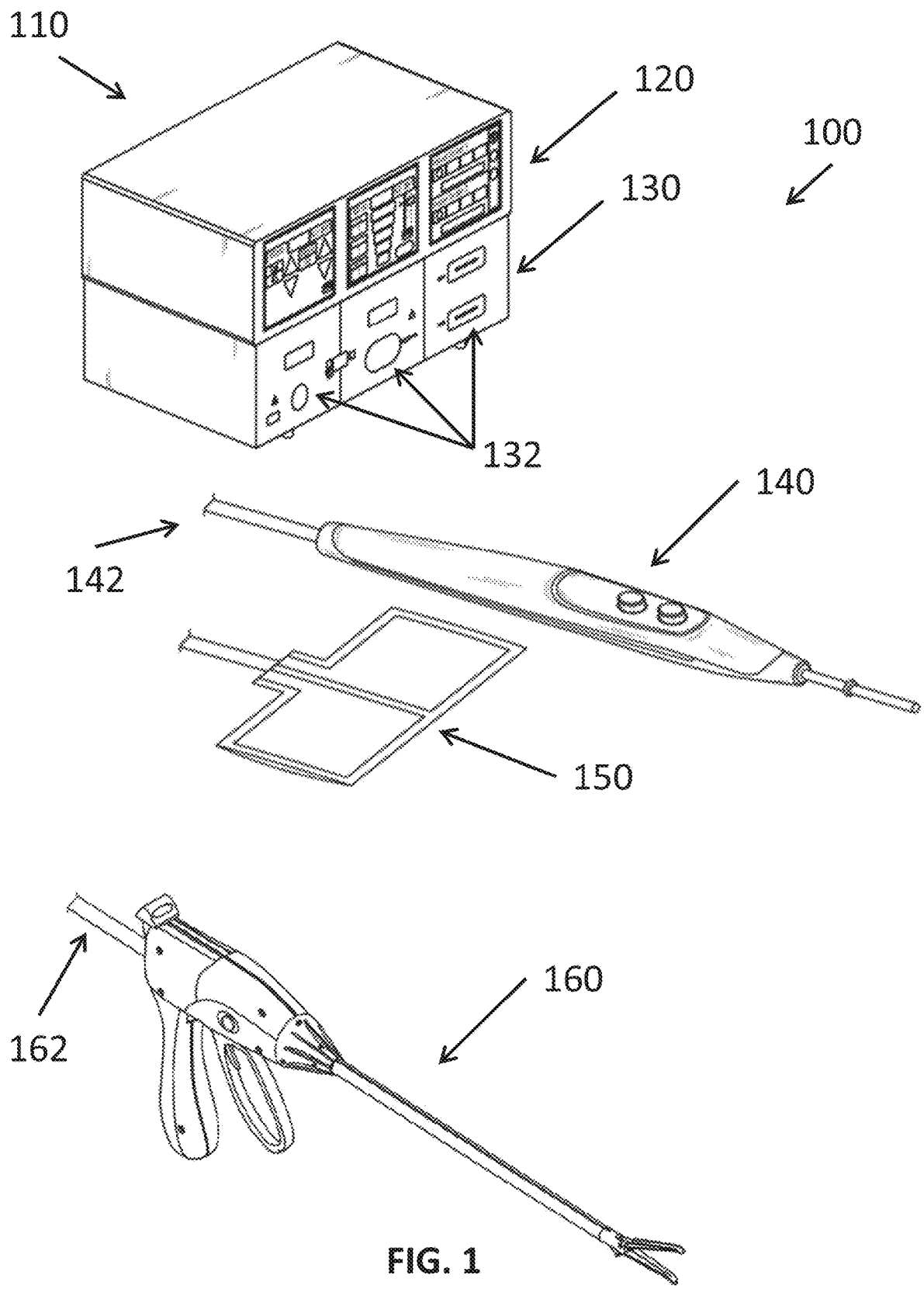
FIG. 1 shows an electrosurgical system including an electrosurgical generator in accordance with embodiments of the present disclosure.

Referring now to FIG. 1, there is shown an electrosurgical system 100 in accordance with embodiments of the present disclosure. The electrosurgical system 100 includes an electrosurgical generator 110 which generates electrosurgical energy to treat a patient. The electrosurgical generator 110 generates an appropriate level of electrosurgical energy based on the selected mode of operation (e.g., cutting, coagulating, ablating, or sealing).

The electrosurgical generator 110 includes a control interface 120, which includes suitable user controls (e.g., buttons, activators, switches, or touch screens) for providing control parameters to the electrosurgical generator 110. These controls allow the user to adjust parameters of the electrosurgical energy (e.g., the power level or the shape of the output waveform) so that the electrosurgical energy is suitable for a particular surgical procedure (e.g., coagulating, ablating, tissue sealing, or cutting).

The electrosurgical generator 110 further includes an instrument interface 130, which has various types of ports 132 corresponding to a variety of electrosurgical instruments.

The electrosurgical system 100 may further include a monopolar electrosurgical instrument 140 having an electrode for treating tissue of the patient (e.g., an electrosurgical cutting probe or ablation electrode) and having a corresponding return pad 150. The monopolar electrosurgical instrument 140 and the return pad 150 can both be connected to the electrosurgical generator 110 via the ports 132. When the monopolar electrosurgical instrument 140 is connected to the electrosurgical generator 110, the electrosurgical generator 110 may power the monopolar electrosurgical instrument 140, which then applies electrosurgical energy to tissue. At least part of the electrosurgical energy then returns to the electrosurgical generator 110 through the return pad 150. The return pad 150 provides sufficient contact area with the patient's tissue so as to minimize the risk of tissue damage due to the electrosurgical energy applied to the tissue.

The electrosurgical system 100 may include a bipolar electrosurgical instrument 160, as shown in FIG. 1. When the bipolar electrosurgical instrument 160 is connected to the electrosurgical generator 110 via one of the ports 132, the electrosurgical generator 110 powers the bipolar instrument 160, which applies electrosurgical energy to the tissue of interest through one prong of the forceps. At least part of the electrosurgical energy returns to the electrosurgical generator 110 through the other prong of the forceps.

The electrosurgical instruments 140 and 160 may also include user controls. In addition, the electrosurgical generator 110 may include one or more display screens for displaying a variety of information related to the operation of the electrosurgical generator 110 (e.g., intensity settings and treatment complete indicators).

When an electrosurgical instrument 140, 160 is connected to the electrosurgical generator 110, leakage current may be drawn from the electrosurgical generator 110 because of parasitic capacitance in the cables 142, 162 of the electrosurgical instruments 140, 160. In various embodiments, cables 142, 162 may be separable from the electrosurgical instruments 140, 160 and can be connected to the electrosurgical generator 110 separately from the electrosurgical instruments 140, 160.

Even when the electrosurgical instrument 140, 160 and cable 142, 162 are not connected to the electrosurgical generator 110, there can be leakage current within the electrosurgical generator 110 because of parasitic capacitance from cables within the electrosurgical generator 110. As used herein, internal cable compensation refers to cable compensation for cables within the electrosurgical generator 110, and external cable compensation refers to cable compensation for cables external to the electrosurgical generator 110. Thus, the electrosurgical generator 110 of the present disclosure has the capability to compensate for the internal and external cable parasitics by utilizing the internal and external cable compensation, respectively.

As will be described below, internal cable compensation for the electrosurgical generator 110 may be pre-configured at the manufacturing time. Because internal cable compensation parameters are unlikely to change, they can be stored within the electrosurgical generator 110 and used on demand. In contrast, the parasitic capacitance of external cables can vary based on the type of inserted instrument or cable and the replacement of an instrument or cable with a different instrument or cable over time. In various embodiments, parameters for external cable compensation can be static based on the type of inserted instrument or cable. In various embodiments, parameters for external cable compensation can be estimated periodically as the external cable compensation is being performed.

Figure 2:
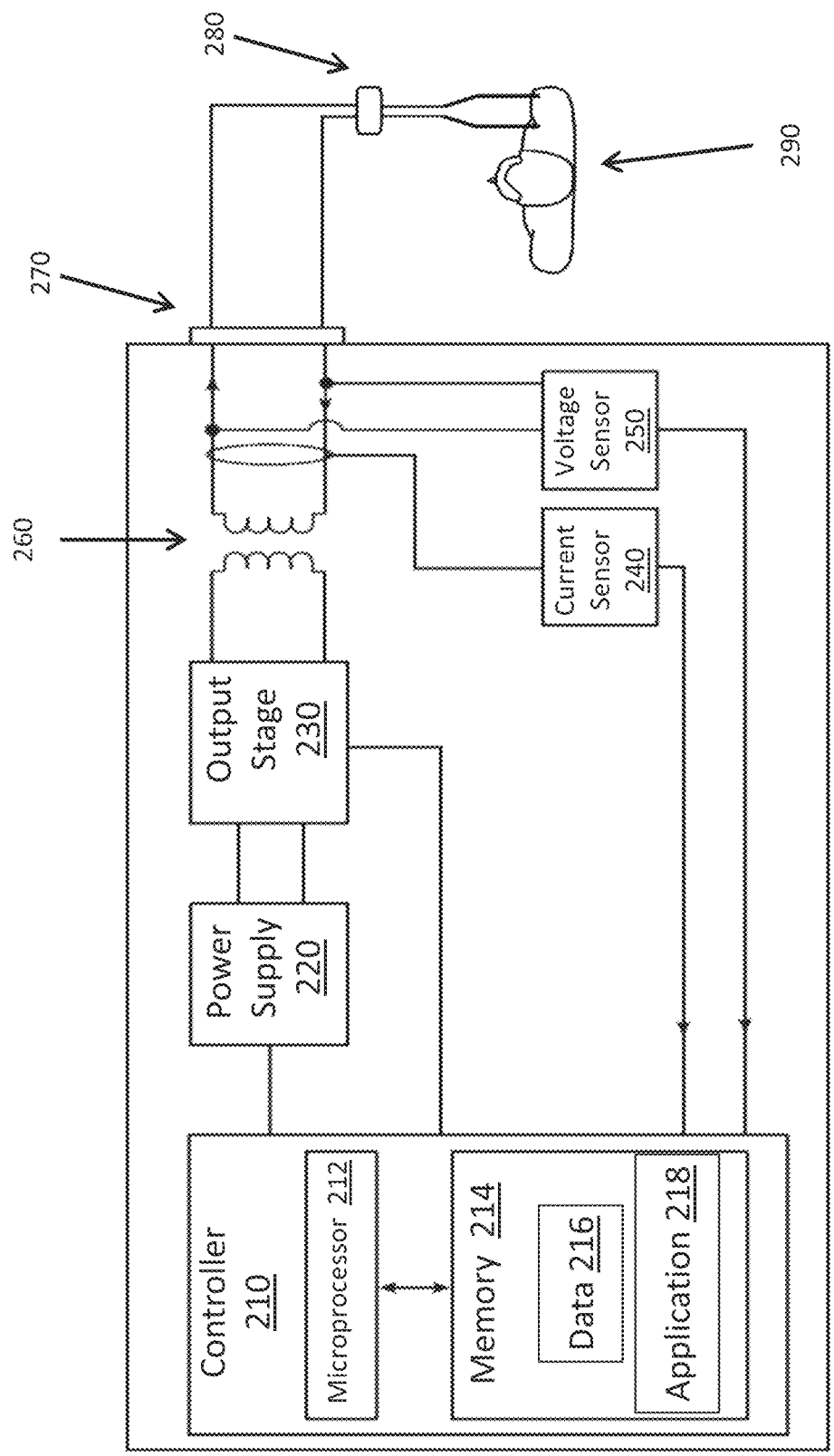
FIG. 2 shows a block diagram of the components of the electrosurgical generator in the electrosurgical system of FIG. 1 in accordance with embodiments of the present disclosure.

FIG. 2 shows a block diagram of components of the electrosurgical generator 200 according to embodiments of the present disclosure. The electrosurgical generator 200 includes a controller 210, a power supply 220, an output stage 230, and an output port 270, among other things. The power supply 220 may be a high voltage direct current (DC) power supply connected to an alternating current (AC) source and provides high voltage DC power to the output stage 230, which converts the high voltage DC power into treatment energy having particular frequency or other characteristics and delivers the treatment energy to the output port 270 through an isolation transformer 260. In various embodiments, the output stage 230 can include an H-bridge that drives a tank. Other embodiments are contemplated and will be recognized by persons skilled in the art.

The output stage 230 is configured to provide a plurality of different electrosurgical waveforms according to different modes selectable by a user at the electrosurgical generator. For example, the output stage 230 can provide electrosurgical waveforms having specific duty cycles, peak voltages, and/or crest factors, among other characteristics, according to the selected mode. The electrosurgical waveforms may be based on other parameters or characteristics not expressly enumerated herein, and such parameters will be recognized by persons skilled in the art.

The controller 210 may control the power supply 220 to adjust a power level of the power supplied to the output stage 230 and to control the output stage 230 to adjust a duty cycle, an operating frequency, and/or an output power level of the resulting electrosurgical waveforms. The controller 210 includes a microprocessor 212 and a memory 214 operably connected to the microprocessor 212. In various embodiments, the microprocessor 212 may be replaced with, for example, any logic processor (e.g., control circuit), field programmable gate array, digital signal processor, and/or combinations thereof.

The memory 214 may store data 216 and applications 218, which can be machine instructions executable by the microprocessor 212. The data 216 may include operational parameters related to the operation of the electrosurgical generator 200, such as internal cable compensation and external cable compensation parameters and any information used by the electrosurgical generator 200. Based on the data 216 and the applications 218 stored in the memory 214, the microprocessor 221 can control the functionalities and operation of the electrosurgical generator 200. For example, the functionalities or methods described below may be implemented by the data 216, the applications 218, and the microprocessor 212.

In various embodiments, the memory 214 may include, without limitation, random access memory (RAM), magnetic disks, magnetic tape, solid state memory, optical discs (CD, DVD, etc.), flash memory, read-only memory (ROM), and/or electrically erasable programmable ROM (EEPROM), among others. The list of memory types is exemplary and other types of memory are contemplated to be within the scope of the present disclosure.

With continuing reference to FIG. 2, the electrosurgical generator 200 may include a current sensor 240, a voltage sensor 250, and a transformer 260. The current sensor 240 is coupled to the secondary of the transformer 260 and measures the current at the secondary of the transformer 206. The voltage sensor 250 is also coupled to the secondary of the transformer 260 and measures the voltage at the secondary of the transformer 260. In an aspect, a plurality of voltage sensors and current sensors are provided for redundancy in case of failure of individual sensors. Various components of the electrosurgical generator 200 may be disposed on a printed circuit board (PCB), including the controller 210, the output stage 230, and the current and voltage sensors 240 and 250. In the embodiment of FIG. 2, it is beneficial to locate the current and voltage sensors 240, 250 at the secondary of the isolation transformer 260, which is closer to the output port 270 and to the patient tissue 290 and reduces issues relating to compensating for various non-linear effects of the isolation transformer 260.

The current and voltage sensors 240 and 250 provide the sensed voltage and current signals, respectively, to the controller 210, which may adjust an output level of the power supply 220 and/or the output stage 230 in response to the sensed voltage and current signals. The controller 210 also receives input signals from the input controls of the electrosurgical generator 200 via the control interface 120 of the electrosurgical generator 110. As will be described below herein, the controller 210 may use the sensed voltage and current signals to determine whether an external cable has been coupled or uncoupled from the output port 270. Additionally, the controller 210 may control internal cable compensation and external cable compensation to control the power delivered to the tissue 290. In accordance with embodiments of the present disclosure, the controller 210 can determine whether a cable has been coupled or uncoupled from the output port 270 based on measurements from the current and voltage sensors 240, 250 and based on internal cable compensation parameters, which will be described in connection with FIGS. 3-8. When the controller 210 determines that the cable is removed from the output port 270, the controller 210 may direct the power supply 220 to stop supplying power. The controller 210 can control other aspects of the electrosurgical generator 200, which persons skilled the art will recognize.

Figure 3:
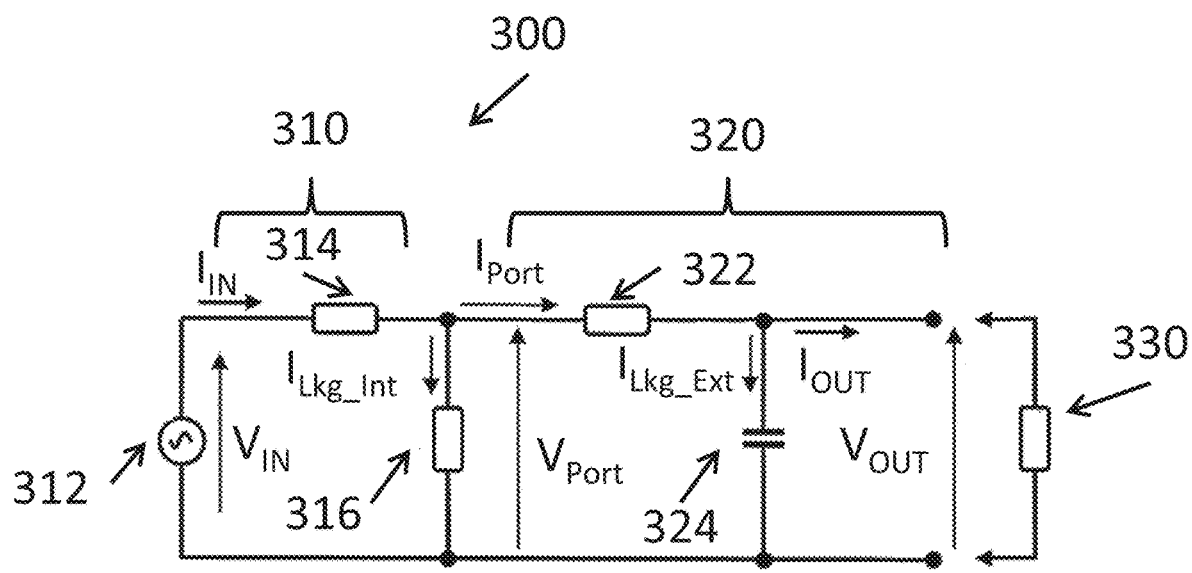
FIG. 3 shows a circuit representation of cables of the electrosurgical system, in connection with cable compensation in accordance with embodiments of the present disclosure.

Referring now to FIG. 3, there is shown a circuit representation of cables of the electrosurgical system, in connection with cable compensation in accordance with embodiments of the present disclosure. The circuit diagram 300 has a first portion 310 that includes a circuit representation of a cable within an electrosurgical generator and a second portion 320 that includes a circuit representation of an external cable. The first portion 310 includes a voltage source 312, an electrical element 314 that represents resistance and/or inductance of an internal cable, and a capacitance 316 that represents parasitic capacitance of the internal cable. In various embodiments, the electrical element 314 can represent a capacitance, that represents internal blocking capacitors, combined with an inductance and resistance. For simplicity, the electrical element 314 will hereafter be referred to as impedance 314, although it will be understood that element 314 can represent inductance and resistance, or capacitance combined with inductance and resistance. The impedance 314 is denoted as $Z_{Src\_Int}$, and the capacitance 316 has impedance denoted as $Z_{Lkg\_Int}$.

The second portion 320 includes an electrical element 322 and a parasitic capacitance of an external cable. For simplicity, the electrical element 322 will hereafter be referred to as resistance 322, although it will be understood that element 322 can also represent inductance and resistance. The resistance 322 has impedance denoted as $Z_{Src\_Ext}$, and the capacitance 324 has impedance denoted as $Z_{Lkg\_Ext}$. FIG. 3 illustrates the situation when the external cable is connected to the electrosurgical generator, thereby connecting the internal cable (first portion 310) to the external cable (second portion 320). Also illustrated is a load 330 at the opposite end of the external cable/second portion 320, which has an impedance denoted as $Z_{Out}$.

The voltage source 312 supplies a voltage $V_{In}$ and a current $I_{In}$. The voltage $V_{In}$ is the voltage supplied to the input of the internal cable and is controlled by the electrosurgical generator. In contrast, the current $I_{In}$ that is supplied to the input of the internal cable depends on the current demanded by the electrosurgical equipment and the load 330. The current $I_{In}$ is divided into an internal leakage current $I_{Lkg\_Int}$, which is current that leaks through the internal capacitance 316, and $I_{Port}$, which is current that flows through the output port to the external cable. The voltage across the parasitic capacitance 316/output port is $V_{Port}$.

In accordance with aspects of the present disclosure, the purpose of internal cable compensation is to determine $I_{Port}$ and $V_{Port}$ given a known $I_{In}$ and $V_{In}$, taking into account the impedance 314 and the parasitic capacitance 316.

In various embodiments, $I_{Port}$ and $V_{Port}$ can be determined based on $V_{In}$ and $I_{In}$ using a matrix computation as shown below:

$$\begin{bmatrix} V_{Port} \\ I_{Port} \end{bmatrix} = \begin{bmatrix} A_{11} & A_{12} \\ A_{21} & A_{22} \end{bmatrix} \cdot \begin{bmatrix} V_{In} \\ I_{In} \end{bmatrix}. \tag{1}$$

The two-by-two matrix in equation (1) is referred to herein as internal compensation matrix, A. As described below, values in the internal compensation matrix, $A_{11}$, $A_{12}$, $A_{21}$, and $A_{22}$, are based on the impedance $Z_{Src\_Int}$ and the impedance of the internal capacitance $Z_{Lkg\_Int}$.

In particular, according to circuit analysis:

$$V_{In} = V_{Port} + I_{In} Z_{Src\_Int} \tag{3}$$

and $$I_{In} = I_{Lkg\_Int} + I_{Port} \quad (4).$$

Since $I_{Lkg\_Int}$ is equal to $$\frac{V_{Port}}{Z_{Lkg\_Int}},$$

equations (3) and (4) become:

$$V_{In} = \quad (3')$$
$$V_{Port} + (I_{Lkg\_Int} + I_{Port})Z_{Src\_Int} = V_{Port} + \left(\frac{V_{Port}}{Z_{Lkg\_Int}} + I_{Port}\right)Z_{Src\_Int} =$$
$$\left(1 + \frac{Z_{Src\_Int}}{Z_{Lkg\_Int}}\right)V_{Port} + Z_{Src\_Int}I_{Port}$$

and $$I_{In} = \frac{V_{Port}}{Z_{Lkg\_Int}} + I_{Port}. \quad (4')$$

Thus, the following equation (5) can be obtained:

$$\begin{bmatrix} V_{In} \\ I_{In} \end{bmatrix} = \begin{bmatrix} 1 + \frac{Z_{Src\_Int}}{Z_{Lkg\_Int}} & Z_{Src\_Int} \\ \frac{1}{Z_{Lkg\_Int}} & 1 \end{bmatrix} \cdot \begin{bmatrix} V_{Port} \\ I_{Port} \end{bmatrix}, \quad (5)$$

where $Z_{Src\_Int}$ and $Z_{Lkg\_Int}$ are the parameters described above. By inverting the two-by-two matrix in equation (5), the following internal compensation matrix A can be obtained:

$$\begin{bmatrix} V_{Port} \\ I_{Port} \end{bmatrix} = \begin{bmatrix} 1 & -Z_{Src\_Int} \\ -\frac{1}{Z_{Lkg\_Int}} & 1 + \frac{Z_{Src\_Int}}{Z_{Lkg\_Int}} \end{bmatrix} \cdot \begin{bmatrix} V_{In} \\ I_{In} \end{bmatrix}. \quad (6)$$

As described above, the internal cable compensation parameters $Z_{Src\_Int}$ and $Z_{Lkg\_Int}$ are generally stable and unlikely to vary, and can be determined at the manufacturing stage and stored in the electrosurgical generator. The voltage $V_{In}$ is measured by the voltage sensor (FIG. 2, 250), and the current $I_{In}$ is measured by the current sensor (FIG. 2, 240). As can be readily seen by equation (6), when $I_{In} = I_{Lkg\_Int}$, then equation (6) yields $I_{Port} = 0$. That is, any component of $I_{In}$ that is attributable to the parasitic capacitance of the internal cable is removed when determining $I_{Port}$. Accordingly, application of internal cable compensation to determine $I_{Port}$ and $V_{Port}$ based on $V_{In}$ and $I_{In}$ can be achieved using equation (6).

Turning now to external cable compensation, the purpose of external cable compensation is to determine $I_{Out}$ and $V_{Out}$ based on $V_{Port}$ and $I_{Port}$, taking into account the external cable resistance 322 and the external parasitic capacitance 324. In various embodiments, $I_{Out}$ and $V_{Out}$ can be determined as shown below:

$$\begin{bmatrix} V_{Out} \\ I_{Out} \end{bmatrix} = \begin{bmatrix} B_{11} & B_{12} \\ B_{21} & B_{22} \end{bmatrix} \cdot \begin{bmatrix} V_{Port} \\ I_{Port} \end{bmatrix}. \quad (2)$$

The two-by-two matrix in equation (2) is referred to herein as external compensation matrix, B.

Values of the external compensation matrix, $B_{11}$, $B_{12}$, $B_{21}$, and $B_{22}$, are based on the impedance of the external cable resistance $Z_{Src\_Ext}$ and the impedance of the external cable capacitance $Z_{Lkg\_Ext}$, and are determined in the same manner described above for internal cable compensation. In particular, the external compensation matrix values are:

$$\begin{bmatrix} V_{Out} \\ I_{Out} \end{bmatrix} = \begin{bmatrix} 1 & -Z_{Src\_Ext} \\ -\frac{1}{Z_{Lkg\_Ext}} & 1 + \frac{Z_{Src\_Ext}}{Z_{Lkg\_Ext}} \end{bmatrix} \cdot \begin{bmatrix} V_{Port} \\ I_{Port} \end{bmatrix}. \quad (7)$$

The external cable compensation parameter $Z_{Lkg\_Ext}$ can vary and will be described below in connection with FIG. 4. The voltage $V_{Port}$ and the current $I_{Port}$ are determined using internal cable compensation. The external cable compensation parameter $Z_{Src\_Ext}$ is the impedance of the external cable resistance, which is generally stable and unlikely to change and can be determined during the manufacturing stage of the external cable. In various embodiments, the electrosurgical generator can obtain the value of $Z_{Src\_Ext}$ from the external cable. In various embodiments, the value of $Z_{Src\_Ext}$ can be manually entered into the electrosurgical interface. Accordingly, application of external cable compensation to determine $I_{Out}$ and $V_{Out}$ based on $V_{Port}$ and $I_{Port}$ can be achieved using equation (7).

Figure 4:
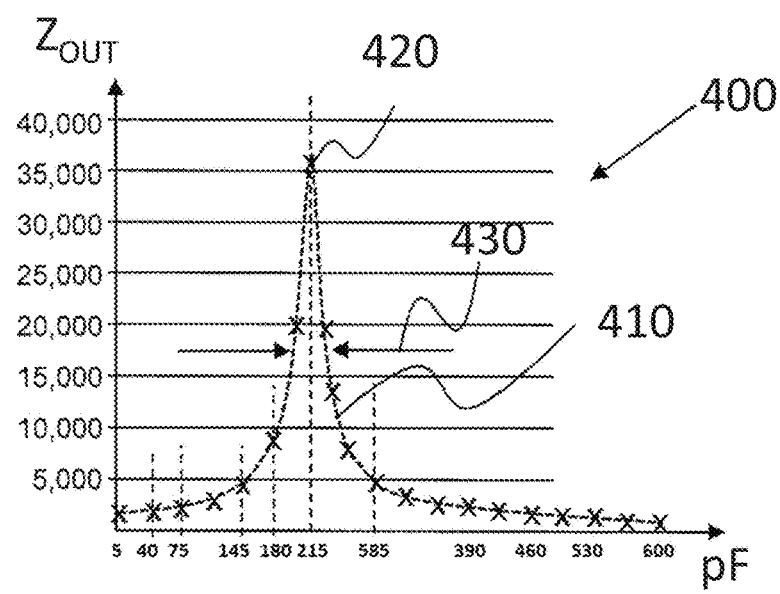
FIG. 4 shows a graph of an external cable compensation sweep in accordance with embodiments of the present disclosure.

Referring now to FIG. 4, a process of estimating the external cable parasitic capacitance will now be described. As mentioned above, the leakage capacitance of the external cable varies based on the configuration, orientation, and positioning of the cable. In an aspect, the leakage capacitance of the cable may be estimated by sweeping potential capacitances $C_{Cable}$ of the cable, such as capacitance 324 of FIG. 3. FIG. 4 shows a capacitance-impedance plot 400 illustrating potential capacitance $C_{Cable}$ (e.g., 324, FIG. 3) of the cable and corresponding perceived load impedance $Z_{Out}$ based on a sweeping method in accordance with an embodiment of the present disclosure.

The horizontal axis of the capacitance-impedance plot 400 shows potential capacitance values $C_{Cable}$ to test against the cable capacitance 324 in pico Farad (pF). The vertical axis indicates perceived load impedance values in ohms ($\Omega$) when the external circuit is open or when the load 330 is not connected to the cable. Sweeping values of potential capacitances $C_{Cable}$ may be performed in the open circuit state in order to ensure that, for any given input voltage $V_{In}$, the output current $I_{Out}$ resulting from $V_{In}$ reflects the leakage capacitance $C_{Cable}$, and is not affected by extraneous impedance (e.g., the load 330).

A capacitance $C_{Cable}$ may be swept across a number of potential capacitance values, and the corresponding output impedance $Z_{Out}$ may be calculated for each potential capacitance value. Referring to the capacitance-impedance plot 410, a potential capacitance value $C_{Cable}$, 5 pF, may result in approximately 2 K$\Omega$ for $Z_{Out}$, 145 pF may result in approximately 5K$\Omega$, 200 pF may result in approximately 20K$\Omega$, and 215 pF may result in approximately 35K$\Omega$, and so on. This process is described in U.S. Pre-Grant Publication No.

2016/0081739A1, the entire contents of which are hereby incorporated herein by reference.

The maximum among the output impedances, Zmax, which is shown at the apex point 420, may be derived by using any suitable mathematical or digital signal processing methods. Based on the sweeping method illustrated in the capacitance-impedance plot 410, Zmax is approximately 35KΩ, and the corresponding capacitance value $C_{Cable}$ resulting in Zmax is approximately 215 pF. Zmax at the apex point 420 is conspicuous, which makes it discernible, and hence detectable or identifiable.

The capacitance value, which results in the maximum output impedance Zmax at the apex point 420 of the capacitance-impedance plot 410, may be assigned as the estimated leakage capacitance (e.g., 324, FIG. 3) of the external cable after the sweeping process. The impedance of the external leakage capacitance $Z_{Lkg\_Ext}$ can then be computed from the external leakage capacitance, as is known by persons skilled in the art. This parameter can then be used in equation (7) for external cable compensation.

Accordingly, what have been described above are methods for performing internal cable compensation and external cable compensation for an electrosurgical system. The following sections will describe systems and methods for detecting whether an external cable has been coupled to or uncoupled from the electrosurgical generator when a cable-detection switch is unavailable or inoperative.

Figure 5:
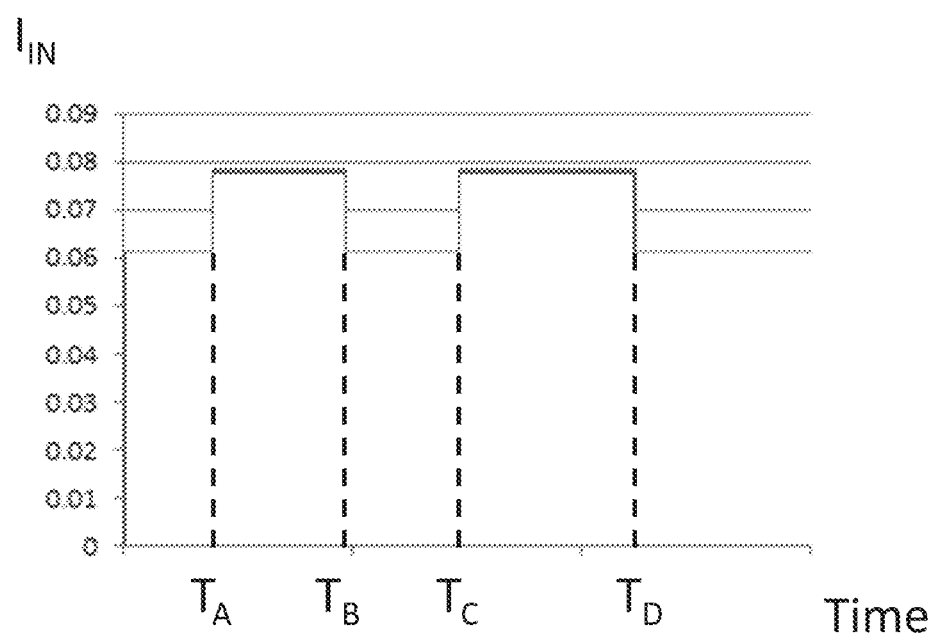
FIG. 5 shows a graph of a supplied current when no cable compensation is applied, in accordance with embodiments of the present disclosure.
Figure 6:
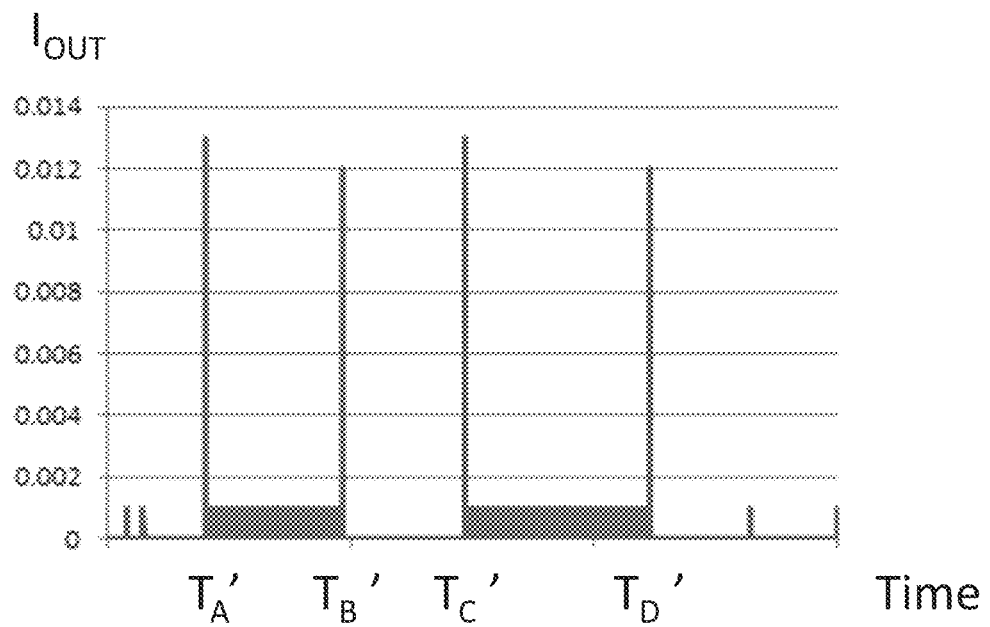
FIG. 6 shows a graph of estimated current exiting an external cable when internal and external cable compensation are applied, in accordance with embodiments of the present disclosure.
Figure 7:
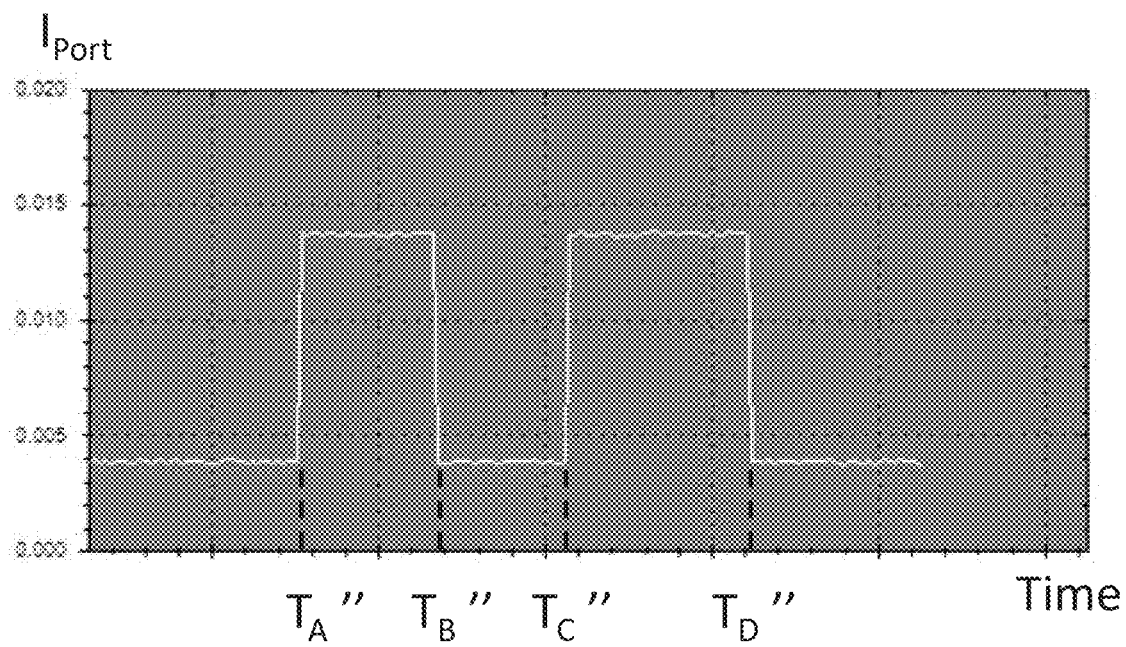
FIG. 7 shows a graph of estimated current entering an external cable when internal cable compensation is applied without external cable compensation, in accordance with embodiments of the present disclosure.

FIGS. 5-7 show various current graphs corresponding to external cable insertion and removal events. In particular, FIG. 5 shows variations of current $I_{In}$ without applying any internal or external cable compensation; FIG. 6 shows variations of the current $I_{Out}$ and the effect of applying both internal and external cable compensation; and FIG. 7 shows variations of the current $I_{Port}$ when applying only internal cable compensation without applying external cable compensation.

Referring to FIG. 5, there is shown variations of the current $I_{In}$ measured at the output stage without applying any internal or external cable compensation. The vertical axis represents amount of the current as a root-mean square value, and the horizontal axis represents time.

During the period between 0 to $T_A$, the external cable is not connected to the output port of the electrosurgical generator, and the measured current $I_{In}$ is about 60 mA. When the external cable is connected to the output port at time $T_A$, current $I_{In}$ increases to 80 mA, and when the external cable is removed from the output port at time $T_B$, current $I_{In}$ decreases back down to 60 mA. In the same way, current $I_{In}$ increases to 80 mA at time $T_C$ when the external cable is re-connected to the output port and decreases back down to 60 mA when the external cable is removed again from the output port at time $T_D$.

In various embodiments, the current difference of 20 mA may be sufficient for detecting an insertion or removal of an external cable to or from the output port of the electrosurgical generator. This current difference can vary dependent on the type or model of the electrosurgical system, the shunt capacitances of the cables, and/or the lengths of the cables. For example, different cables with different shunt capacitances may change the current difference, such that a short cable with low shunt capacitance may reduce the change in current. Although the current difference may differ in different embodiments, the current $I_{In}$ measured at the output stage of the electrosurgical generator, without applying internal and external cable compensation, may be used to detect an insertion or removal of the cable in various embodiments.

In an aspect, the electrosurgical generator may store a predetermined current difference threshold for current $I_{In}$ that is configured to detect an insertion or removal of the external cable. Whenever an external cable is connected to the electrosurgical generator, the electrosurgical generator may use the predetermined current difference threshold value to detect an insertion or removal of the cable.

Referring now to FIG. 6, there is shown variations of the computed current $I_{Out}$ when applying internal and external cable compensation. The vertical axis represents amount of current as a root-mean square value, and the horizontal axis represents time. The current spikes in FIG. 6 are attributable to artifacts of applying the previous external cable capacitance sweep when conditions change, such as when the cable is inserted or removed.

During a period from 0 to $T_A'$, the computed current $I_{Out}$ appears to be very minimal or close to zero mA, when the external cable is not connected to the electrosurgical generator. At time $T_A'$ when the external cable is inserted, the current $I_{Out}$ temporarily spikes up to about 13 mA. This rise of the current $I_{Out}$ occurs because time is needed for the external cable capacitance sweep to be performed to determine the leakage capacitance of the attached cable, which is to be used in the external compensation algorithm. When the external cable capacitance is being determined, the external cable compensation is not yet performed, so the computed current $I_{Out}$ is not yet fully compensated and thus is not accurate. After the external cable capacitance sweep is completed, the external cable compensation is then performed to remove any current component attributable to the external cable parasitic capacitance, as shown in the period from $T_A'$ and $T_B'$, when the current $I_{Out}$ is computed to be about 1 mA.

Similarly, at time $T_B'$ when the external cable is removed from the electrosurgical generator, the computed current $I_{Out}$ temporally spikes up to about 12 mA because the external cable compensation is no longer correct, and then returns down to about zero mA after the external cable compensation is corrected. This same phenomenon occurs during the period when the external cable is attached at time $T_C'$ and when it is removed at time $T_D'$. In various embodiments, the current spikes at the edges of the external cable insertion and removal events can be used by the electrosurgical generator to detect such events. In various embodiments, the electrosurgical generator may need to know whether the system powered up with an external cable connected or without an external cable connected.

Referring to FIG. 7, there is shown variations of the current $I_{Port}$ when applying internal cable compensation but not applying external cable compensation in accordance with embodiments of the present disclosure. The vertical axis represents amount of current as a root-mean square value, and the horizontal axis represents time.

During a period from 0 to $T_A''$ when the external cable is not connected to the electrosurgical generator, the current $I_{Port}$ is determined by equation (6) to be about 4 mA. It is important to recognize that $I_{Port}$ is not an actual measured current at the output port of the electrosurgical generator. Rather, it is an estimated current in FIG. 3 that is derived by measuring an actual current $I_{In}$ at the output stage of the electrosurgical generator and removing any current component attributable to internal cable parasitic effects. Thus, when $I_{Port}$ is determined to be non-zero when no external cable is attached, this suggests intuitively that $I_{In} > I_{Lkg\_Int}$. That is, other components different from the internal cable are also drawing current. Such other components may be, for example, other parasitic effects within the electrosurgical generator that are not represented in FIG. 3. In various embodiments, such other components can include a cable adaptor that is connected to the output port of the electrosurgical generator, as will be explained further in connection with FIG. 9. After time $T_A''$ when the external cable is inserted into the electrosurgical generator, the current $I_{Port}$ rises to about 14 mA and is maintained until time $T_B''$ when the external cable is removed. The current $I_{Port}$ differs by about 10 mA between external cable insertion and removal, such as shown between times $T_A''$ and $T_B''$ and again at times $T_C''$ and $T_D''$.

In various embodiments, this difference in the current $I_{Port}$ may be used to detect an insertion and removal of the external cable. For example, a 10 mA rise in the current $I_{Port}$ can be determined to be an external cable insertion event, and a 10 mA decrease in the current $I_{Port}$ can be determined to be an external cable removal event. The current difference of 10 mA is provided as an example and is not meant to be limiting, and other threshold values are contemplated.

In various embodiments, an absolute current threshold can be used to determine whether there is an external cable insertion or removal event. For example, the current threshold value can be a value between 5 mA and 10 mA, inclusive, such as 8 mA. In this manner, when the current $I_{Port}$ rises above the current threshold, it can be determined to be a cable insertion event, and when the current $I_{Port}$ decreases below the current threshold, it can be determined to be a cable removal event, as described in more detail below in connection with FIGS. 8A and 8B.

Figure 8A:
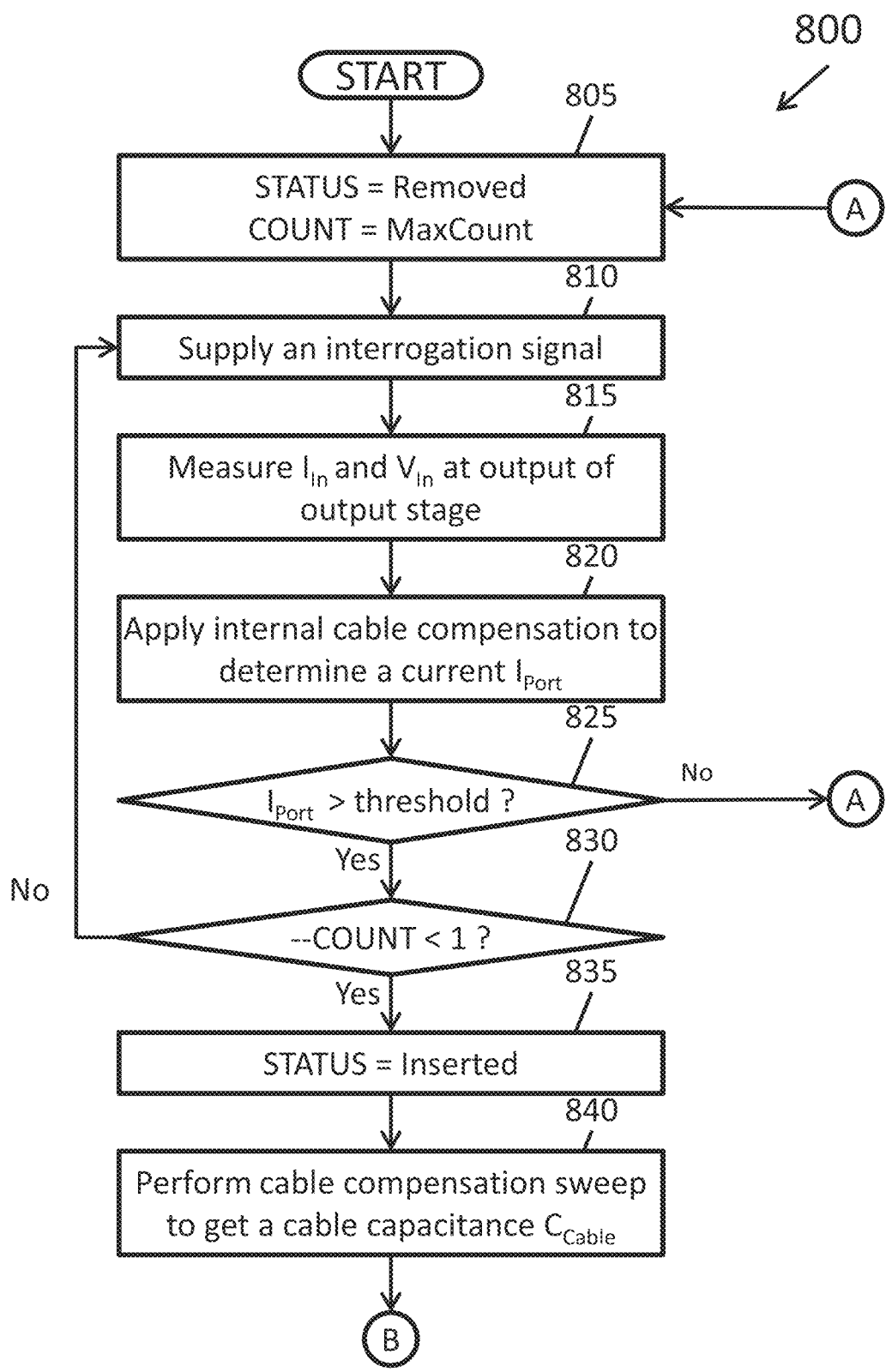
FIGS. 8A and 8B show flow diagrams of a method of detecting insertion or removal of a cable to or from an electrosurgical generator in accordance with embodiments of the present disclosure.
Figure 8B:
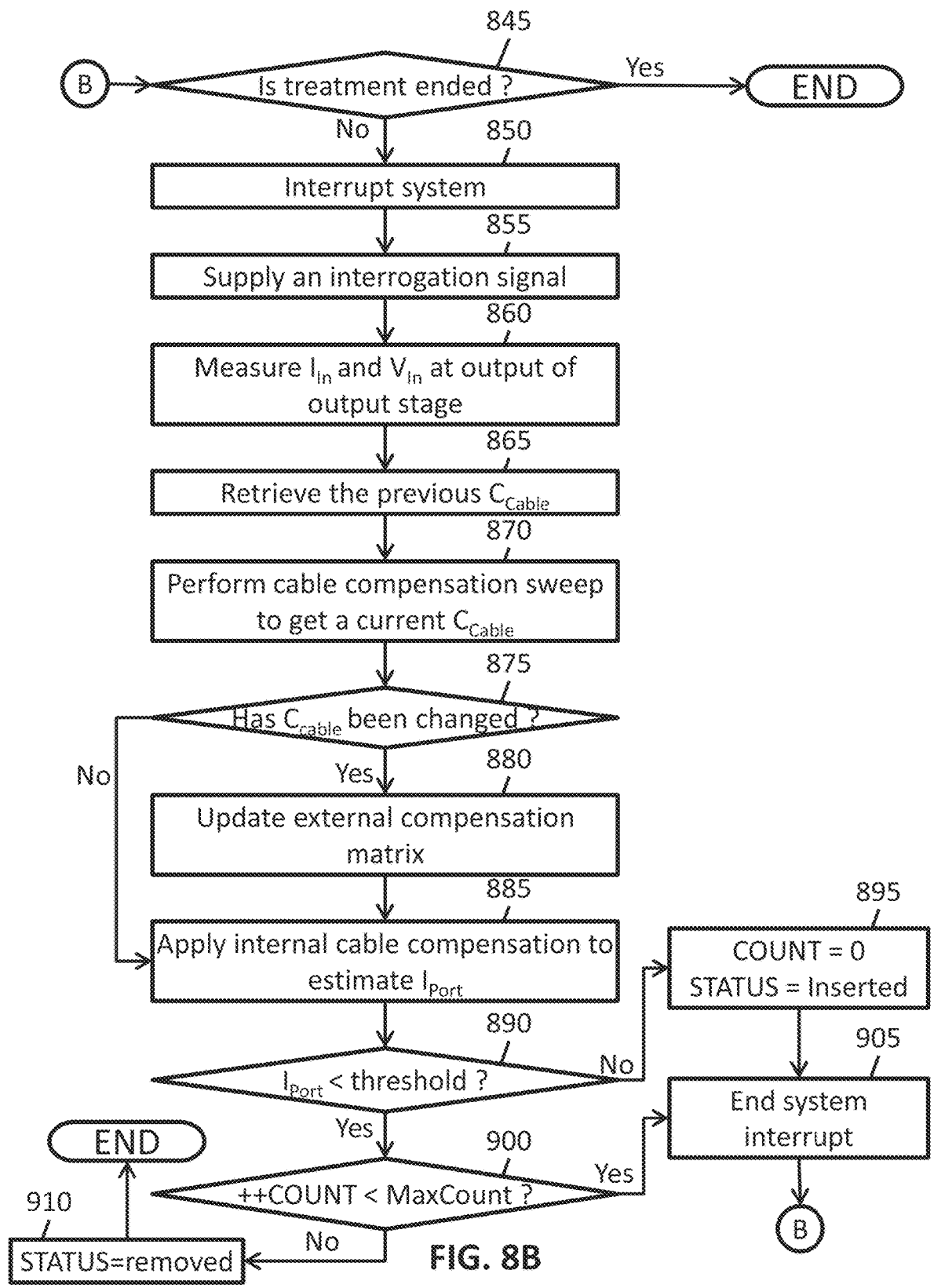

FIGS. 8A and 8B are flowcharts illustrating a method 800 for detecting an insertion or removal of a cable to or from an electrosurgical generator in accordance with embodiments of the present disclosure. The method 800 may start when an electrosurgical generator is powered on and end when the electrosurgical generator is powered off or when the external cable is removed. In step 805, the electrosurgical generator is powered up and parameters relating to cable detection may be set or reset. For example, the parameter for STATUS of the external cable connectivity is set to "removed," reflecting that the external cable is not connected. The electrosurgical generator can include another parameter indicated as COUNT, which is used to count a time delay before the value of the STATUS parameter can be changed. Initially, the value of COUNT can be set to a maximum time delay value denoted as MaxCount.

In step 810, the electrosurgical generator supplies a voltage signal which will be referred to as an "interrogation signal." In an aspect, the interrogation signal may have preset characteristics, such as a preset frequency and/or amplitude.

After the interrogation signal is supplied, voltage and current sensors at the output of the output stage of the electrosurgical generator measure the voltage $V_{In}$ and current $I_{In}$ that result from the interrogation signal, in step 815. $V_{In}$ and $I_{In}$ represent voltage and current conveyed by the output stage of the electrosurgical generator to the internal cable.

In step 820, the controller of the electrosurgical generator may apply internal cable compensation, as described above herein, to determine the current $I_{Port}$.

In step 825, the current, $I_{Port}$ is compared with a current threshold value. If $I_{Port}$ is not greater than the current threshold, the method 800 returns to step 805, in which COUNT is reset to the MaxCount and the STATUS is set to "removed."

If the current $I_{Port}$ is greater than the current threshold, then COUNT is decremented in step 830. If COUNT is not zero, the method 800 returns to step 810. If COUNT is zero, then the $I_{Port}$ has remained above the current threshold for the entire time delay, and STATUS is set to "inserted," reflecting the determination that the external cable has been connected, in step 835. The time delay implemented by the COUNT parameter may be used to discount technical glitches or sudden changes in configuration of the external cable that result in a temporary change in the current $I_{Port}$. In this way, the status of the cable is identified with greater confidence.

In the illustrated embodiment, after the insertion of the cable is detected, in step 835, the method 800 performs the external cable capacitance sweep, as described above herein, in step 840. The method 800 then proceeds to step 845 of FIG. 8B.

In step 845, it is determined whether treatment of the patient is completed. The treatment may be completed, for example, when the generator is instructed to power down. If the treatment is completed, the method 800 ends. In various embodiments, after treatment is completed in step 845, the method 800 may restart and be performed again.

If the treatment is not completed, in step 845, the system is interrupted in step 850. In various embodiments, the system interrupt can be a software interrupt that suspends the software process of the current generator operation and executes steps 855-900 of FIG. 8B. Once those steps are completed, the interrupt can end, in step 905, and the suspended software process can be reactivated. After the system interrupt in step 850, the interrogation signal is supplied in step 855. The voltage and current sensors measure voltage $V_{In}$ and current $I_{In}$ at the output stage in step 860.

In step 865, a previously stored leakage capacitance of the external cable, $C_{Cable}$, is retrieved. In a case when no leakage capacitance of the external cable is stored, a default value may be used as the previously stored leakage capacitance of the external cable.

In step 870, a cable capacitance sweep is performed to obtain an updated leakage capacitance of the external cable, in the manner described above herein in connection with FIG. 4.

The updated leakage capacitance $C_{Cable}$ is compared with the previously stored leakage capacitance $C_{Cable}$ in step 875. If the updated leakage capacitance $C_{Cable}$ is different from the previously stored leakage capacitance $C_{Cable}$, the updated leakage capacitance $C_{Cable}$ may replace the previously stored leakage capacitance $C_{Cable}$ value and can be used to update the external cable compensation matrix in step 880. In various embodiments, the updated leakage capacitance $C_{Cable}$ can replace the previously stored leakage capacitance $C_{Cable}$ when their difference is greater than a predetermined threshold. In various embodiments, the updated leakage capacitance $C_{Cable}$ can replace the previously stored leakage capacitance $C_{Cable}$ when there is any amount of difference in their values.

If there is no change between the updated leakage capacitance $C_{Cable}$ and the previously stored leakage capacitance $C_{Cable}$, the method proceeds directly from step 875 to step 885. In step 885, internal cable compensation is applied to estimate the current $I_{Port}$.

In step 890, the current $I_{Port}$ is compared with the current threshold, as in step 825. When it is determined that $I_{Port}$ is not less than the current threshold, COUNT is reset to zero and the STATUS is maintained as "inserted" in step 895. And then, the system interrupt ends in step 905, and the method returns to step 845.

If the current $I_{Port}$ is less than the current threshold in step 890, the COUNT parameter is incremented and compared with MaxCount in step 900. If COUNT is less than Max-Count, then the system interrupt ends and the method returns to step 845.

If COUNT is determined to be equal to MaxCount in step 900, then $I_{Port}$ has stayed below the current threshold for the entire time delay implemented by the COUNT parameter. Then, STATUS is updated to indicate that the cable is removed from the output port of the electrosurgical generator, and the method ends. However, the method of FIGS. 8A and 8B can be restarted and executed periodically to detect another insertion of an external cable.

In an aspect, the system interrupt at step 850 can be performed periodically, such as every 25 milliseconds. In various embodiments, the interrogation voltage signal at step 855 can have the same characteristics as the treatment energy or can have different characteristics, such as the same or different frequency or amplitude, as long as $I_{Port}$ generally remains greater than the current threshold when the external cable is connected to the electrosurgical generator. Additionally, the interrogation voltage signal at step 855 may be supplied at certain times when the electrosurgical instrument is coupled to a patient. In various embodiments, the interrogation voltage signal at step 855 can be configured to have non-negative impact on the patient or to be non-harmful to the patient. In various embodiments, the interrogation voltage signal at step 855 can be configured to have a therapeutic effect on the patient.

What have been described above are systems and methods for detecting insertion or removal of an external cable from an electrosurgical generator when a cable detection switch is unavailable or inoperable. The following paragraphs, in connection with FIG. 9, describe a particular embodiment when a cable detection switch may be unavailable because of a port adaptor.

Figure 9:
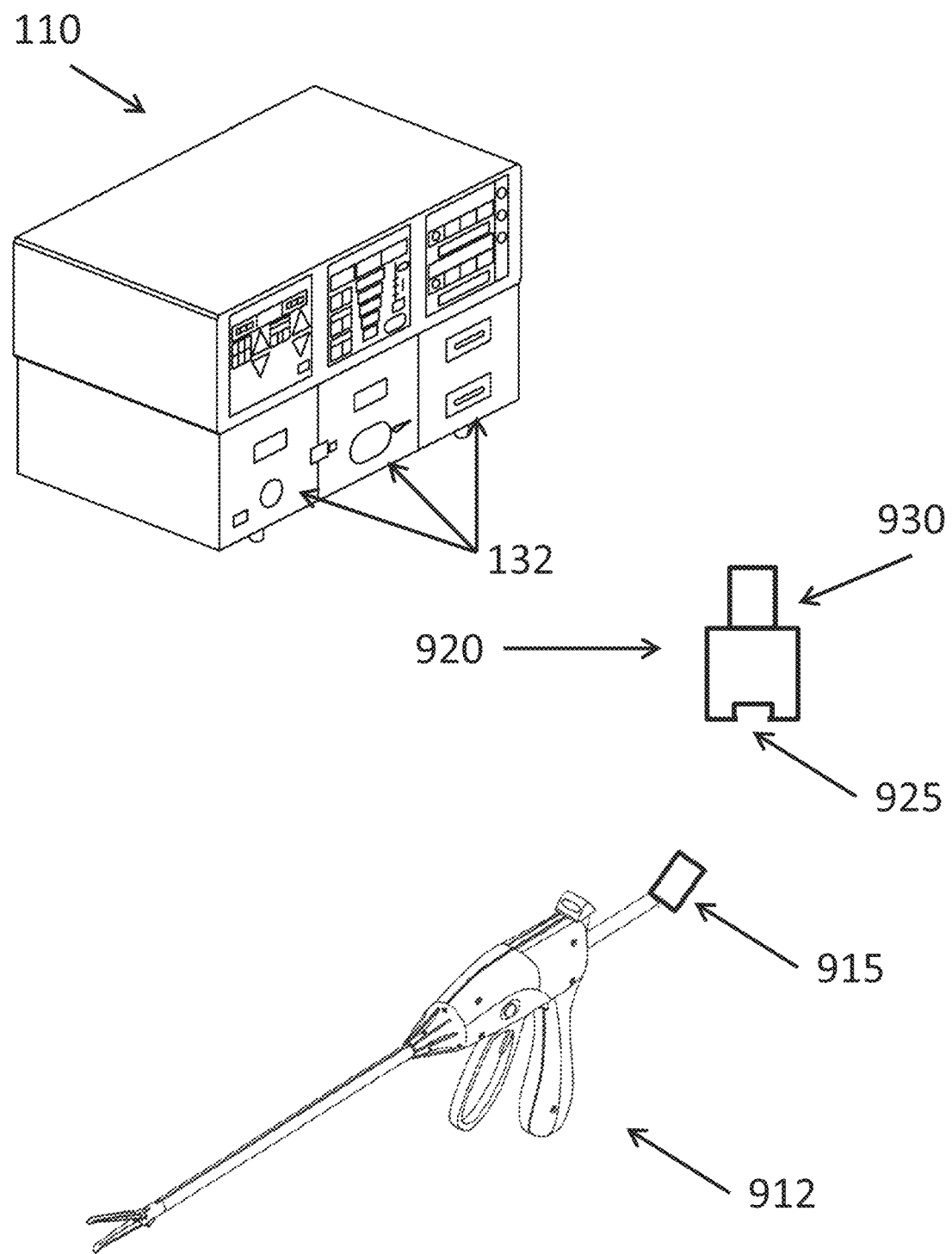
FIG. 9 shows an electrosurgical system including an adaptor in accordance with embodiments of the present disclosure.

FIG. 9 shows a system configuration in which an adaptor 920 is used as an intermediate connector between the electrosurgical generator 110 and an electrosurgical instrument 912 in accordance with an aspect of the present disclosure. In various embodiments, the adaptor 920 may be used when the electrosurgical generator 110 and the electrosurgical instrument 912 are made by different manufacturers. In various embodiments, when an insertion portion 915 of the electrosurgical instrument 912 does not match with a port 132 of the electrosurgical generator 110 but the instrument and the generator are otherwise compatible, the adaptor 920 may be used. The adaptor 920 includes an instrument connector 925 and an electrosurgical generator connector 930. The instrument connector 925 is configured to mate with the insertion portion 915 of the electrosurgical instrument 912 and the electrosurgical generator connector 930 is configured to mate with the port 132.

When the adaptor 920 is connected to the electrosurgical generator 110, the cable detection switch of the electrosurgical generator 110 is used by the adaptor 920. In that situation, the electrosurgical generator 110 has no physical mechanism to detect an insertion or removal of the external cable into the adaptor 920. According to embodiments of the present disclosure, the disclosed systems and methods may be used to detect an insertion or removal of the external cable from the adaptor 920.

Although the illustrative embodiments of the present disclosure have been described herein with reference to the accompanying drawings, it is to be understood that the disclosure is not limited to those precise embodiments, and that various other changes and modification may be effected therein by one skilled in the art without departing from the scope or spirit of the disclosure.

What is claimed is:

1. An electrosurgical generator comprising:
   a power supply;
   an output port configured to receive an external cable;
   internal cabling having a first end portion connected to the output port and a second end portion connected to the power supply;
   a current sensor configured to measure current at the second end portion of the internal cabling;
   a voltage sensor configured to measure voltage at the second end portion of the internal cabling;
   one or more processors; and
   at least one memory coupled to the one or more processors and storing instructions which, when executed by the one or more processors, cause the electrosurgical generator to:
   supply power from the power supply;
   receive a current measurement from the current sensor;
   receive a voltage measurement from the voltage sensor;
   apply an internal cable compensation, without applying an external cable compensation, to estimate a current at the output port based on the current measurement and the voltage measurement; and
   determine coupling or uncoupling of the external cable from the output port based on the estimated current.

2. The electrosurgical generator according to claim 1, wherein the internal cabling includes a resistance, an inductance, and a capacitance, and
   wherein the at least one parameter corresponds to the resistance, the inductance, and the capacitance of the internal cabling within the electrosurgical generator.

3. The electrosurgical generator according to claim 1, wherein the instructions, when executed by the one or more processors, further cause the electrosurgical generator to compare the estimated current at the output port to a current threshold.

4. The electrosurgical generator according to claim 3, wherein coupling or uncoupling of the external cable from the output port is determined based on the comparison.

5. The electrosurgical generator according to claim 3, wherein in comparing the estimated current at the output port, the instructions, when executed by the one or more processors, further cause the electrosurgical generator to determine that the estimated current at the output port is greater than the current threshold.

6. The electrosurgical generator according to claim 5, wherein the external cable is determined to be coupled to the output port when the estimated current at the output port is greater than the current threshold for a predetermined period of time.

7. The electrosurgical generator according to claim 3, wherein in comparing the estimated current at the output port, the instructions, when executed by the one or more processors, further cause the electrosurgical generator to determine that the estimated current at the output port is less than the current threshold.

8. The electrosurgical generator according to claim 7, wherein in the external cable is determined to be uncoupled from the output port when the estimated current at the output port is less than the current threshold for a predetermined period of time.

9. The electrosurgical generator according to claim 8, further comprising an adaptor configured to be connected between the output port and the external cable.

10. The electrosurgical generator according to claim 9, wherein the estimated current at the output port is an estimate of current passing through the adaptor.

11. The electrosurgical generator according to claim 3, wherein the supplied power from the electrosurgical generator is an interrogation voltage signal.

12. The electrosurgical generator according to claim 11, wherein a frequency of the interrogation voltage signal is substantially the same as a frequency of a therapeutic treatment energy that is to be supplied by the electrosurgical generator.

13. The electrosurgical generator according to claim 12, wherein an amplitude of the interrogation voltage signal is less than an amplitude of the therapeutic treatment energy.

* * * * *